United States Patent [19]

Yom et al.

[11] Patent Number: 5,585,276
[45] Date of Patent: Dec. 17, 1996

[54] MEDIUM AND METHOD FOR BLOTTING MACROMOLECULES

[75] Inventors: Heng-Cherl Yom; Robert D. Bremel, both of Madison, Wis.

[73] Assignee: Wisconsin Alumni Research Foundation, Madison, Wis.

[21] Appl. No.: 216,880

[22] Filed: Mar. 23, 1994

Related U.S. Application Data

[63] Continuation of Ser. No. 41,277, Mar. 29, 1993, which is a continuation of Ser. No. 698,624, May 10, 1991.

[51] Int. Cl.$^6$ ..................... G01N 33/543; G01N 33/558; G01N 33/544; G01N 33/53
[52] U.S. Cl. ..................... 436/518; 436/514; 436/530; 436/543; 435/7.92; 435/7.9
[58] Field of Search ..................... 436/514, 530, 436/518, 543; 435/7.92, 7.9

[56] References Cited

PUBLICATIONS

Stott, D. I., J. Immunol Meth 119:153–187. (1989).
Minamide et al., Anal Biochem 190, 66–70 (1990).
Murthy et al., Anal Biochem 64:18–29 (1975).
Conn, et al., *Outlines of Biochemistry* 5/E, 244–245, John Wiley & Sons, New York (1987).
Freifelder, D., *Molecular Biology* 2d Ed., pp. 133–135, Jones & Bartlett, Boston (1987).
Montgomery and Fu, "Detection of Cellulose–Binding Proteins in Electrophoresis Gels by Filter Paper Affinity Blotting," *Anal. Biochem.*, 174[1]:204–208 (1988).
Stott, D. I., *J. Immunol. Meth.* 117:153–187 (1989).

*Primary Examiner*—Michael P. Woodward
*Attorney, Agent, or Firm*—Quarles & Brady

[57] ABSTRACT

A medium and method for blotting macromolecules is disclosed. The method begins with the separation of macromolecules on a slab gel. Next, a sheet of cellulosic paper is dipped into an alcohol bath. The dipped paper is placed against the slab gel. The paper and the gel are exposed to a means for transferring the macromolecules from the gel onto the paper. In a particularly advantageous embodiment of the method, the paper is dipped into a methanol bath, the transferring means includes an electric field, and the paper is either xerographic paper or cotton bond paper. The present invention is also a medium for blotting macromolecules comprising a piece of cellulosic paper that has been dipped in alcohol.

2 Claims, 2 Drawing Sheets

MEDIUM AND METHOD FOR BLOTTING MACROMOLECULES

This application is a continuation-in-part of application Ser. No. 08/041,277, filed Mar. 29, 1993; which is a continuation of No. 07/698,624 filed May 10, 1991.

FIELD OF THE INVENTION

The field of the present invention is methods and mediums for blotting macromolecules after electrophoretic separation on a slab gel. In particular, the field is mediums suitable for Western blot analysis.

BACKGROUND ART

Blotting techniques are widely used in biochemical analyses to identify regions of protein-antibody binding or nucleic acid-nucleic acid hybridization. Blotting techniques begin with the electrophoresis of macromolecules, either proteins or nucleic acids, on a solid support. Electrophoresis is a technique that depends on the relative mobility of charged particles, in this case macromolecules, under an electric field in a solid support. This support is usually an agarose slab gel or acrylamide slab gel. A solution containing the macromolecules of interest is loaded into one end of the slab gel. An electric field is created in the slab gel and causes the macromolecules to travel into the slab gel. The goal of electrophoresis in these cases is to create a distributional pattern of macromolecules within the solid support.

There are various ways that these macromolecules can be distributed. Macromolecules travel in an electric field with a speed proportional to the size of the molecule. In separating populations of molecules that have different sizes but carry similar charges, such as populations of RNA or DNA, the smaller molecules will travel farther on the solid gel support than the larger molecules. Therefore, the molecules separate on the slab gel on the basis of size.

Another way to separate molecules on a slab gel is on the basis of their charge. Populations of protein molecules differ as to the net charge that each molecule carries in a solution of given pH. If during the electrophoretic procedure a pH gradient is formed across the solid gel support, molecules will migrate into the gel until the molecules reach their isoelectric point in the pH gradient. At the isoelectric point, the molecule carries no charge. Because different protein molecules have different isoelectric points, populations of protein molecules can be distributed in the slab gel via the charge they carry.

It is possible to combine the two techniques of charge and size separation. The technique of two-dimensional gel electrophoresis involves two different electrophoretic separations of protein molecules. The molecules are separated in one dimension by their isoelectric point. The molecules are then separated in the second dimension according to their molecular size.

It is often advantageous to expose these separated macromolecules to other components and analyze the binding of components to the separated macromolecules. For example, a particular messenger RNA might have been isolated and cloned, and a scientist might be interested in isolating the gene corresponding to that messenger RNA. Analyzing which DNA fragment in a restriction enzyme digest of genomic DNA could hybridize to a cDNA clone created from this messenger RNA would facilitate the isolation of the gene.

The technique of Southern blotting allows one to analyze these DNA-DNA hybridizations. In a Southern blotting procedure, DNA fragments are first electrophoretically distributed within a slab gel. Typically, the slab gel is immersed in a basic solution that denatures the DNA fragments. The slab gel is then laid on a stack of buffer-soaked filter paper. A blotting medium, which will receive the macromolecules as they leave the slab gel, is placed against the gel. A stack of dry filter papers is placed on top of this blotting medium.

Capillary action draws the buffer from the buffer-soaked filter paper through the gel and through the blotting medium. The buffer flows into the dry filter papers stacked on top of the blotting medium. DNA fragments are transferred from the slab gel onto the blotting medium. The fragments stick to the blotting medium and are not transferred to the dry filter papers because the pore size of the blotting medium is such that small molecules pass through but larger macromolecules can be trapped. The blotting medium now contains a copy of the DNA distribution pattern of the slab gel. This macromolecule-laden blotting medium is called a "blot."

Blots can be created in ways other than through capillary action. Recently blots have been created by a process called "electroblotting." An electric field is created across the slab gel and blotting medium and the macromolecules are electrophoresed onto the blotting medium. This procedure is usually quicker than the capillary blotting procedure.

The blot is usually placed in a plastic pouch with a solution of radioactive probe, either DNA or RNA. Molecular hybridization will occur with those portions of the blotted DNA molecules that have a nucleotide sequence which is sufficiently complementary to the radioactive DNA or RNA probes. The blotting medium can then be washed, dried, and exposed to x-ray film. When the film is developed, it will retain an image of the hybridization pattern of the radioactive probe. Therefore, the particular fragment in a DNA digest that hybridizes with this particular probe can be identified via its location on this developed x-ray film.

In another example, electrophoretically separated proteins are often incubated with antibody-containing solutions, with the purpose of analyzing the position of the protein molecules that specifically bind to the antibodies. This technique is referred to as "Western blotting". Radiolabelled antibodies can reveal the location of antibody-protein binding. Additionally, locations of specific binding can be visualized in other ways. A common technique is to conjugate an identifiable enzyme to the antibody. For instance, peroxidase can be attached to the bound antibody. If one incubates this antibody-laden blot in a solution containing a peroxidase substrate and an oxidizable chromogen, the areas containing peroxidase will change color and will be easily visualized.

The blotting medium is typically a nitrocellulose filter, commercially available from many sources. Nitrocellulose filters are flat sheets made from cellulose nitrate, a nitric acid ester of cellulose. This filter binds DNA strongly, and the DNA can be permanently fixed to the nitrocellulose filter by baking at approximately 80° C. Proteins and nucleic acids are adsorbed to the surface of nitrocellulose by electrostatic and hydrophobic interaction. Nitrocellulose filters are very widely used for blotting techniques, but they are mechanically fragile and expensive.

Nylon was introduced in blotting mediums because of its greater mechanical strength and higher protein binding capability. However, nylon membranes are not compatible with any protein stain except the biotin/avidin system. Recently, hydrophobic PVDF (polyvinylidene difluoride)

membrane has been introduced. This membrane has mechanical strength, high binding capacity and good compatibility with most Western blot procedures. This material, however, is somewhat expensive and not without staining artifacts. For example, in our lab we have used PVDF membranes to blot milk proteins. We frequently find a white spot during immuno-staining. These white spots are an artifact of the PVDF membrane.

What is needed in the art of macromolecule blotting is a blotting medium that is easy to prepare, inexpensive, compatible with standard macromolecule visualization methods, and mechanically strong enough to withstand manipulation in blotting procedures.

SUMMARY OF THE INVENTION

The present invention is a method of macromolecular blotting. This method begins with the separation of macromolecules on a slab gel. Next, a sheet of cellulosic paper is dipped into an alcohol bath. The dipped paper is placed against the slab gel. The paper and the gel are exposed to a means for transferring the macromolecules from the gel onto the paper.

In a particularly advantageous embodiment of the method, the paper is dipped into a methanol bath, the transferring means includes an electric field, and the paper is either xerographic paper or cotton bond paper.

The present invention is also a method of quantitating a protein sample. This method begins with the separation of a protein sample on a slab gel. Next a sheet of cellulosic paper is dipped into an alcohol bath. The dipped paper is placed against the slab gel. The cellulosic paper and the gel are exposed to a means for transferring the molecules from the gel onto the paper. The protein-laden blot is exposed to an antibody-containing solution. The antibodies in the antibody-containing solution are allowed to bind to the blot, and the blot is exposed to a means for indicating the location of antibody binding. The antibody binding is analyzed such that a quantitative determination of protein concentration may be obtained.

In a particularly advantageous embodiment of the method, the means for indicating the location of antibody binding comprises a colorimetric reaction such that the presence of an antibody is indicated by a stain. Additionally, a digitized image of the stained blot is obtained and analyzed.

The present invention is also a medium for blotting macromolecules comprising a piece of cellulosic paper that has been dipped in alcohol.

It is an object of the present invention to provide a method and medium for blotting macromolecules.

One advantage of the present invention is that the medium for blotting macromolecules is much cheaper than blotting mediums presently available.

Another advantage of the present invention is that the medium for blotting macromolecules is easy to work with and mechanically strong enough to withstand manipulation in blotting procedures.

Another advantage of the present invention is that the blotting medium may be quickly prepared.

Another advantage is that the blotting medium is capable of detecting small amounts of protein.

Another advantage is that the blotting medium is capable of binding macromolecules in such a way that a linear relationship between molecular concentration and staining intensity can be obtained.

Another advantage of the present invention is that the blotting medium is compatible with standard immuno-staining techniques and does not produce artifactual staining.

Other objects, advantages, and features of the present invention will become apparent from the following specification when taken into conjunction with the accompanying figures.

DESCRIPTION OF THE PREFERRED EMBODIMENT

Figure 1:
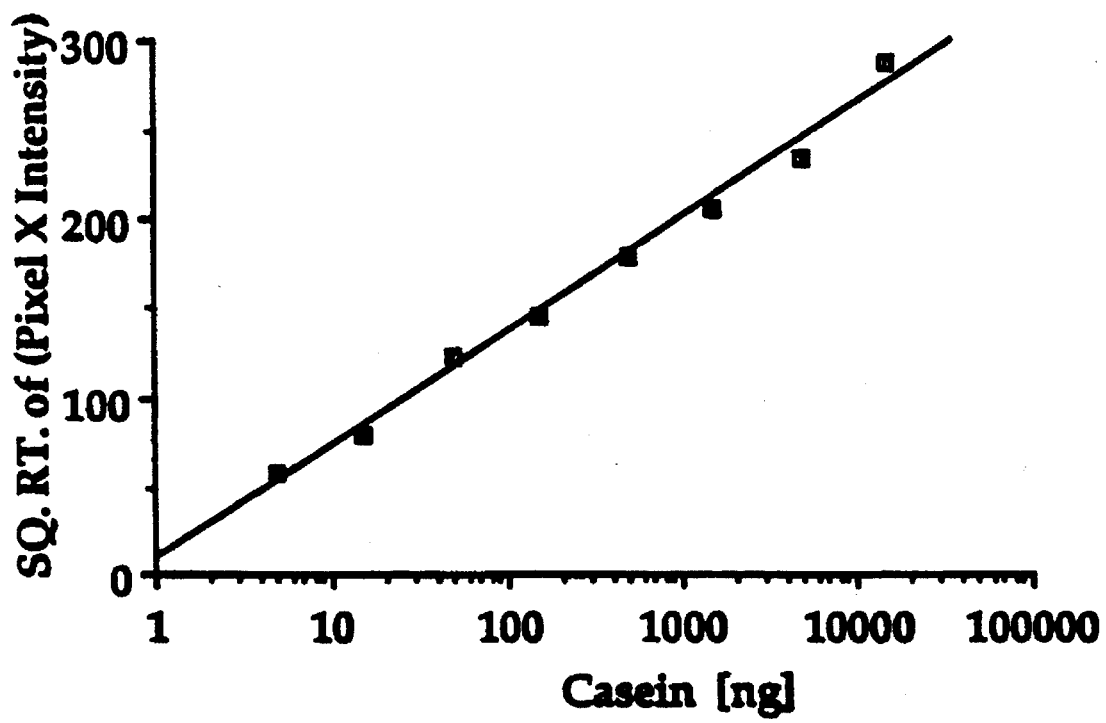
FIG. 1. is a graph of the densitometric analysis of a Western blot. The blot contains a serial dilution of cows' milk (5 ng–1.5 μg). Xerographic paper was used as the blotting medium.

The present invention is a method and a medium for blotting macromolecules. In brief, the method begins with the separation of macromolecules on a slab gel. A sheet of cellulosic paper is prepared by dipping the paper into an alcohol bath. The dipped paper is placed against the slab gel. The slab gel and blotting medium are exposed to a means for transferring the macromolecules from the slab gel to the blotting medium.

The present invention is also a method for quantitating protein concentration. This method involves the steps discussed above plus exposing the blot to an antibody-containing solution, allowing antibodies in the antibody-containing solution to bind to the blot, exposing the antibody-bound blot to a means for indicating the location of antibody binding and analyzing the antibody binding such that a quantitative determination of protein concentration may be obtained.

Molecules are first electrophoretically separated on a slab gel. This may be by one of a number of standard techniques. We chose a 12% SDS-polyacrylamide mini-gel system (described below) because this small gel more rapidly separated our proteins and a 12% gel was the correct percentage to separate proteins of interest. However, we envision that different gel systems, either agarose or acrylimide, would be equally suitable for the method of the present invention.

Material suitable for use as a blotting medium in the present invention is "cellulosic paper." By cellulosic paper, we mean any paper composed primarily of cellulose, such as paper commonly used for writing, typing, printing and photocopying. Two common examples of cellulosic paper are xerographic paper and cotton bond. These papers are inexpensive, of sufficient mechanical strength to withstand the blotting and hybridization procedures, and compatible with standard macromolecular staining techniques. The term "cellulosic paper" does not include papers containing cellulose nitrate, such as nitrocellulose.

It is important to note the transfer side of the blotting medium because this side should be kept face-up throughout all incubation periods. The blotting medium is cut with a template to the size of the slab gel.

Both proteins and nucleic acids are suitable for blotting by the present invention. Our Examples demonstrate reproducible binding of protein molecules. Because both proteins and nucleic acids typically contain a predominantly negative charge and it is this charge that participates in the binding of the macromolecule to the blotting medium, we envision that nucleic acids would behave in a manner similar to proteins.

We chose to dip the paper into methanol. It is essential that the paper be wetted before transfer. Prewetting the paper with methanol was the single most critical step, although the wetting time did not appear to be critical. Without methanol wetting, the proteins did not reproducibly bind to the paper. We speculate that the methanol might wet and expose certain hydrophobic sites on the surface of a paper. However, the exact mechanism by which alcohol wetting creates a suitable blotting medium is poorly understood.

We envision that other chemical solutions will be suitable for producing a blotting medium capable of receiving and binding transferred macromolecules. Alcohols with shorter carbon chains (1–6) are especially envisioned as effective.

The blotting medium is placed next to the slab gel. Typically, the blotting medium is carefully placed on top of the slab gel so that there are no air bubbles between the gel and the paper. The slab gel and blotting medium are exposed to a means for transferring the macromolecules from the slab gel to the blotting medium. This means could be either the standard capillary blotting method, involving buffer soaked filter papers and dry filter papers, or could be by electroblotting methods which employ an electric field across the gel and blotting medium. At this point a macromolecule-laden blotting medium, or "blot", is formed.

Our method for visualizing where antibody-protein binding takes place on the blot is by a version of the standard peroxidase immuno-staining technique (described below). Other standard staining techniques could easily be used. In addition, radiolabelled probes or antibodies could be employed. Radiolabelled probes would be especially effective to visualize nucleic acid binding.

To quantitate a specific protein in a protein sample, one must scan the stained or radiolabelled blot with a means for quantitating the intensity of the stain or radioactive signal. In our Examples, we scanned the peroxidase stained blot with an image scanner and created a digitized image. This digitized image can be analyzed and each protein band integrated. The results of this integration can be compared, either between the different bands on the same blot or to a standard curve, to obtain a quantitative analysis of protein concentration.

EXAMPLES

In the following Examples, we compared the Western blot capabilities of xerographic paper, cotton bond paper, and PVDF membranes. The electrophoresis gel apparatus and system, the antibody incubation and staining, and the analysis of the blot were the same in all of our Examples. We varied our transfer protocol in Example 5c to determine the effect of transfer buffer temperature on blotting capabilities. We also varied our destaining protocol. In our first attempt at blotting with xerographic paper, Example 5a, we omitted the destaining step in order to determine the maximum capability of binding of xerographic paper in a Western blot procedure.

1. Electrophoresis

Proteins were electrophoretically separated on a 1.5 millimeter thick 12% SDS-polyacrylimide gel using a Bio-rad mini gel apparatus (Bio-rad Laboratories, Richmond, Calif.). The gel system was as described by Laemmli, *Nature* 227: 680–685 (1970). The protein samples loaded onto the gel were serial dilutions of cows' milk. Bovine alpha-Sl-casein, one component of cows' milk, ranged from 5 ng to 1.5 mg in the dilutions.

2. Transfer

After electrophoresis, the gel was equilibrated with transfer buffer (25 mM Tris, 192 mM Glycine, pH 8.3) for 5 minutes. The blotting medium was cut to the size of the mini gel and the orientation was marked in pencil. In our Examples, we used xerographic paper, (Xerox 4024 DP 20 lb. paper, Long grain, Stock No. 3R721, Xerox Co., Rochester, N.Y.), cotton bond paper (25% rag, Gilbert Thesis Bond), and PVDF membrane (Immobilon-P, Millipore Corp., Bedford, Mass.) as blotting mediums.

The blotting medium was dipped into 100% methanol for 2 minutes. (The wetting time did not appear to be critical.) The wet blotting medium was equilibrated with transfer buffer for 2 minutes and then placed flat side against the mini gel. The gel and blotting medium were then sandwiched between filter papers. (GB002, Schleicher & Schuell Inc., Keene, N.H.).

In our Examples, the means for transferring the macromolecules from the gel onto the blotting medium was an electric current. Our standard transfer procedure is as follows: The proteins in the gel were electrically transferred to the blotting medium for 1 hour at constant 100 V (starting current ~0.35 amp, finishing current~1.0 amp) while the buffer was cooled by a small ice bucket (Bio-Rad Lab.). When xerographic paper or cotton bond paper were used as blotting mediums, the initial temperature of transfer buffer was 20° C. or room temperature and the final buffer temperature reached 70° C. This is a higher current and temperature than we observed with other membranes, such as PVDF. Most of the heat was generated during the last 10 to 15 minutes of the transfer.

3. Antibody Incubation and Visualization

Our antibody identification technique is a version of the standard peroxidase immuno-staining technique. In brief, an antibody is allowed to bind to the protein we are interested in. This antibody is called the "first antibody." A "second antibody," that will bind to the first antibody, is conjugated with peroxidase. The second antibody is allowed to bind to the first antibody. We then determine the location of peroxidase in the blot.

If peroxidase is incubated in a solution containing peroxidase substrate and a suitable oxidizable chromogen, a brown color will develop on the blot where the original first antibody bound. This brown color can be densitometrically scanned for intensity. The intensity of the brown color will be proportional to the intensity of binding of the first antibody. Therefore, the intensity of the brown color will be proportional to the concentration of the protein that bound to the first antibody.

In our Examples, the first antibody was chicken anti-casein antibody from egg yolks as described by Polson et al., *Immun. Communi.* 9:495–514 (1980). The second antibody was peroxidase labelled-rabbit anti-chicken antibody (Sigma Chemical, St. Louis, Mo.).

Our standard antibody and substrate incubation technique was as follows: After transfer of the macromolecules to the blotting medium, the blot was briefly washed in Western buffer. (Western buffer is 20 mM Sodium phosphate, 120 mM NaCl, 10 mM EDTA, 0.1% gelatin (porcine skin), 0.05% Tween 20, pH 7.2.) The blot was then incubated with a mild shaking motion at 20° C. for 1.5 hour with a 1/1,500 dilution of first antibody (chicken anti-casein antibody) in Western buffer. The blotting medium was kept transfer side up for all incubation periods. After incubation, the blot was briefly washed in Western buffer.

The blot was incubated with a mild shaking motion at 20° C. for 1.5 hr with a 1/5,000 dilution of enzyme-conjugated second antibody (peroxidase labelled-rabbit anti-chicken antibody) in Western buffer and followed by a brief wash in Western buffer. The blots were then incubated at 20° C. for 7 minutes with DAB substrate solution. (DAB substrate solution is 25 mg of 3.3'-diaminobenzidine (DAB), 1 ml of 1% $CoCl_2$, 49 ml Phosphate buffer saline (PBS) pH 7.4, and 0.05 ml of 30% $H_2O_2$.) DAB substrate solution was freshly prepared and added immediately prior to use. The color reaction occurred, and the blot was destained to remove non-specific background stain.

After incubation in the DAB substrate solution, the blot was destained for 5 minutes with a Comassie blue destaining solution (40% methanol/10% acetic acid) to remove background. The method was as follows: Two layers of 3MM filter paper (Whatman, Hillsboro, Oreg.) were saturated with the destaining solution and the excess solution was drained. The blot was carefully placed over the saturated filter paper (transfer side up) for 5 minutes. The blot was then air-dried.

4. Scanning and Analysis of Blot

The dry blot was scanned by an image scanner (MSF-300G, Microtek Lab Inc., Torrance, Calif.) at 100% size with 100 dot/inch resolution. The file was saved in a tagged image file format (TIFF). This scanning created a digitized image of the stained blot which could be analyzed quantitatively.

The digitized image was analyzed using the Collage program (Fotodyne, Milwaukee, Wis.) which allows integration of individual protein bands in the image. Each pixel intensity was transformed by $\log i/i_0$ into optical density, and the average pixel intensity of the background of the image was subtracted. The pixel intensity of each band was integrated individually and plotted as square root of integrated pixel intensity against log of protein concentration.

5. Results of Individual Blotting Experiments a. Detection of Bovine Alpha-S1-casein on Xerographic Paper In our first blotting experiment, we electrophoresed serial dilutions of cow milk (ranging from 5 ng to 1.5 µg of bovine alpha-S1-casein) on our standard gel system. We transferred the proteins from the gel to xerographic paper and treated the blot with the antibody-containing solutions as described above. However, the destaining step was omitted to show the effect of destaining on the background signal.

The M.W. of bovine alpha-S1-casein is 23,000 daltons. However, it has been reported that the protein appears as a 32,000 dalton band on SDS-PAGE system. Our electrophoretic gels showed a large band at the 32,000 dalton position, and we assume that this band represents alpha-S1-casein.

We examined the stained blots and noted that the signal increases with increasing casein concentration. We analyzed the 32,000 dalton band via our standard methods. FIG. 1 is the result of that analysis and shows that the log of the casein concentration is linearly related with the square root of an integrated pixel intensity ($r^2>0.96$). Each point represents a different casein concentration. The linear relationship was observed over the range of casein concentration we tested—5 ng to 1.5 µg. This same relationship was observed in five replicate gels that either contained the same range of protein concentration or a much narrower range of protein concentration (0 to 100 ng). The limit of detectability using xerographic paper as a blotting medium in this particular experiment was 5 ng. We define detectability of a protein as the minimal amount of protein that we can visually detect using the method described above.

b. Detection of Alpha-S1-Casein using Cotton Bond Paper as a Blotting Medium

Our next Western blot employed cotton bond paper (25% mg) prepared by the method described above. Unlike the xerographic paper blot described in Example 5a, the cotton bond paper blot was destained. The limit of detectability was similar with cotton bond and xerographic paper. The limit of detectability with cotton bond paper in this particular experiment was approximately 10 ng. The linear relationship of casein concentration versus image intensity was not different from FIG. 1 ($p<0.01$). The only difference observed between cotton bond and xerographic paper was that the current went much higher, reaching approximately 1.5 Amps at the end of the transfer in comparison to approximately 1.0 Amps in case of xerographic paper. Pre-wetting in 100% methanol was essential and the inclusion of methanol (20% v/v) in the transfer buffer resulted in failure of detection with both xerographic and cotton bond paper.

c. Effect of Transfer Buffer Temperature

We observed that the detectability of bovine alpha-S1-casein varied with the final temperature of the transfer buffer. Therefore, we investigated the effect of the transfer buffer temperature on detectability for both xerographic paper and PVDF. In our first experiment, we compared Western blots using paper and PVDF at 45° C. final transfer buffer temperature. The buffer was kept at 4° C. prior to use, cooled by a small ice bucket during electrical transfer, and allowed to reach 45° C. at the end of transfer. The limit of detectability was 30 ng of bovine alpha-S1-casein with xerographic paper and 100 ng with PVDF.

Figure 2:
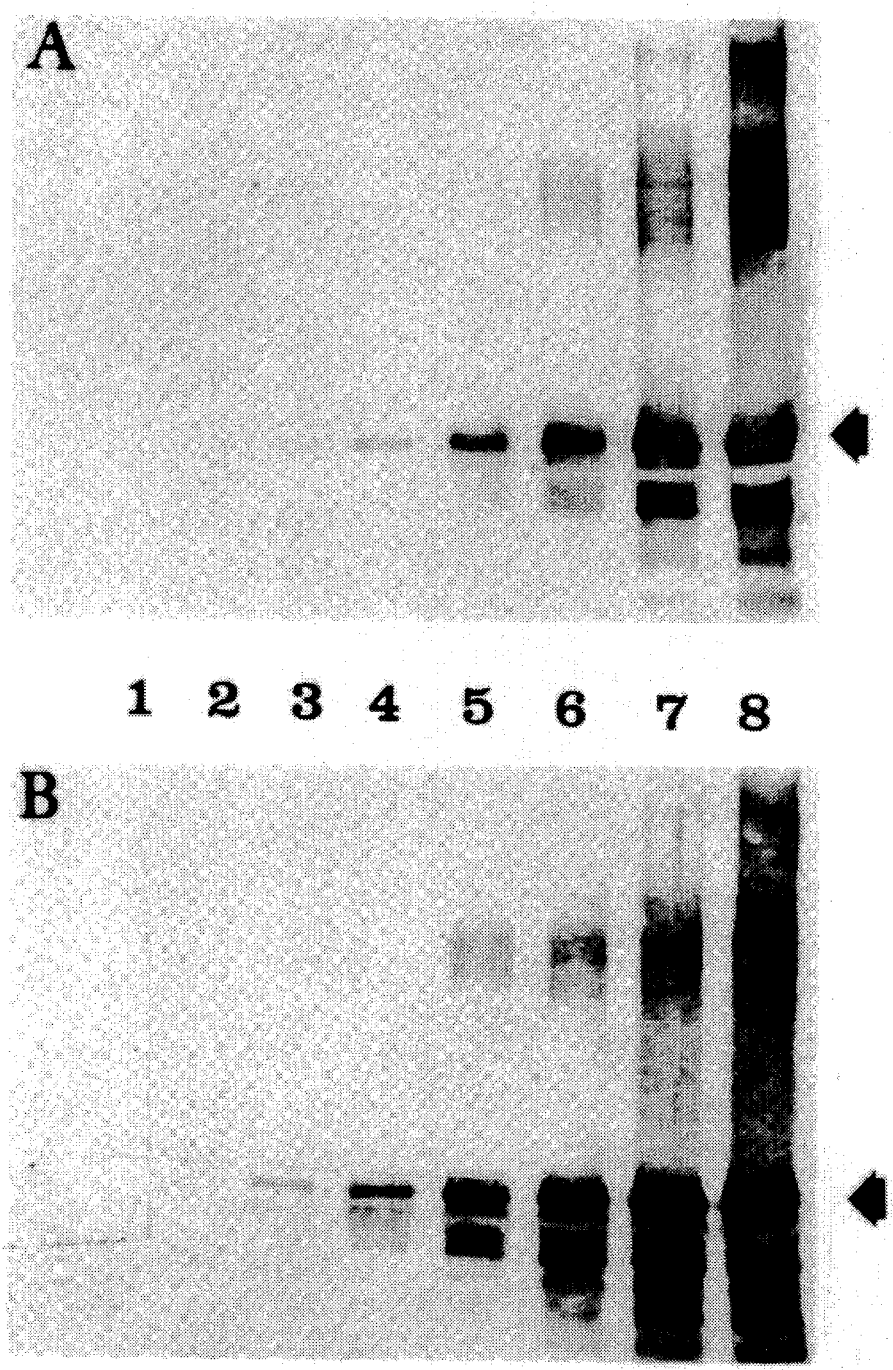
FIG. 2. is a digitized image of two Western blots of a serial dilution of cows' milk at a transfer temperature of 70° C. Blot A is PVDF membrane. Blot B is xerographic paper.

FIG. 2 is a comparison of the digitized version of stained Western blots using xerographic paper and PVDF at 70° C. final transfer buffer temperature. The arrows indicate the migration point of bovine alpha-S1-casein. The buffer was kept at 20° C. prior to use, cooled by a small ice bucket during electrical transfer, and allowed to reach 70° C. at the end of transfer. The limit of detectability in this particular experiment was 10 ng of bovine alpha-S1-casein with xerographic paper and 30 ng with PVDF.

Again referring to FIG. 2, when PVDF was the blotting medium, the lanes with higher protein mass contained white spots inside the bovine alpha-S1-casein bands. This is shown in Lane 7–8 in FIG. 2A. These spots occasionally appear in bands of other hydrophobic proteins when PVDF membrane is used as a blotting medium. These white regions make it impossible to quantitate protein content by scanning densitometry. However, these artifacts were not present in the xerographic paper blot, as shown in FIG. 2B.

The results indicate that the increase in the buffer temperature from 45° C. to 70° C. results in about 3-fold increase in detectability for both xerographic paper and PVDF. Higher signals were observed for xerographic paper compared to those for PVDF, although higher background appeared with xerographic paper. The background was corrected for by subtracting the average pixel intensity of the background using the Collage program.

6. Recovery of added proteins in Western Blot Analysis Using Xerographic Paper

To validate our Western blot assay for estimation of specific proteins, we added a known amount of bovine alpha-S1-casein to transgenic mouse milk containing bovine alpha-Sl-casein secreted as a mouse milk protein and to nontransgenic mouse milk. In this manner, we demonstrated that we are quantitating antibody binding to bovine casein and not artifactual binding.

In lanes 1 through 4 of our standard gel system, we electrophoresed nontransgenic mouse milk plus purified bovine alpha-Sl-casein (0 ng, 25 ng, 50 ng, 100 ng). Since mouse milk contains no bovine casein, Lane 1 would be a negative control. As expected, we saw no stain intensity in Lane 1. Stain intensity increased with increasing amounts of added bovine casein.

For estimation of an unknown sample, an internal standard was included along with the samples. This standard was the casein produced by the transgenic mouse. Lanes 5 through 8 contain transgenic mouse milk plus purified bovine alpha-Sl-casein (0 ng, 12.5 ng, 25 ng, 50 ng). (The transgenic mouse milk in lanes 5 through 8 contained 55 ng bovine alpha-Sl-casein per lane.) Stain intensity increased with increasing amounts of added bovine casein.

We scanned the digitized image of the blot of lanes 5 through 8 and compared the pixel intensity of the gel lanes with added casein to a standard curve. Through this analysis, we determined that recovery was 92.3% for 12.5 ng, 93.4% for 25 ng, and 89.7% for 50 ng.

7. Assay Variation

The replications of lanes within in the same blot showed that coefficient variation (CV) of the intra-assay was 12.4% (n=4). The replications of blots in independent assays showed that CV of the inter-assays was 15.7% (n=4).

Many modifications and variations of these Examples which will still be within the spirit and scope of the invention will be apparent to those with ordinary skill in the art. For example, other inexpensive papers other than xerographic or cotton bond paper may be employed. Additionally, many other gel systems and buffer systems would be equally advantageous. In order to apprise the public of the various embodiments that may fall within the scope of the invention, the following claims are made.

We claim:

1. A method of blotting polypeptide macromolecules comprising
   (a) separating the macromolecules on an SDS-polyacrylamide gel;
   (b) dipping a sheet of cellulosic paper not containing cellulose nitrate in methyl alcohol, the paper selected from the group consisting of xerographic paper and bond paper having cotton content;
   (c) placing the cellulosic paper against the gel;
   (d) exposing the cellulosic paper to the gel under conditions which favor the transfer of the macromolecules from the gel onto the cellulosic paper.

2. A method of quantitating a protein sample comprising;
   (a) separating the proteins in the protein sample on an SDS-polyacrylamide gel;
   (b) dipping a sheet of cellulosic paper selected from the group consisting of xerographic paper and bond paper in methanol;
   (c) placing the cellulosic paper against the gel;
   (d) exposing the cellulosic paper to the gel under conditions which favor the transfer of the proteins from the gel onto the paper, wherein a blot is formed;
   (e) exposing the blot to an antibody-containing solution;
   (f) allowing antibodies in the antibody-containing solution to bind to the blot;
   (g) exposing the antibody-bound blot formed in step (f) to a means for indicating the location of antibody binding; and
   (h) analyzing the antibody binding such that a quantitative determination of protein concentration may be obtained.

* * * * *